United States Patent
Ogata et al.

(10) Patent No.: US 11,913,906 B2
(45) Date of Patent: Feb. 27, 2024

(54) SUBSTANCE DETECTION DEVICE WITH IMPROVED EFFICIENCY

(71) Applicant: I-PEX Inc., Kyoto (JP)

(72) Inventors: Kenji Ogata, Fukuoka (JP); Shogo Kurogi, Fukuoka (JP)

(73) Assignee: I-PEX Inc., Kyoto (JP)

( * ) Notice: Subject to any disclaimer, the term of this patent is extended or adjusted under 35 U.S.C. 154(b) by 469 days.

(21) Appl. No.: 17/278,761

(22) PCT Filed: Aug. 2, 2019

(86) PCT No.: PCT/JP2019/030447
§ 371 (c)(1),
(2) Date: Mar. 23, 2021

(87) PCT Pub. No.: WO2020/066295
PCT Pub. Date: Apr. 2, 2020

(65) Prior Publication Data
US 2022/0042949 A1    Feb. 10, 2022

(30) Foreign Application Priority Data

Sep. 27, 2018  (JP) .................. 2018-182353
Apr. 22, 2019  (JP) .................. 2019-080654

(51) Int. Cl.
*G01N 29/00* (2006.01)
*G01N 29/036* (2006.01)
(Continued)

(52) U.S. Cl.
CPC ....... *G01N 29/036* (2013.01); *G01N 29/2437* (2013.01); *G01N 33/0027* (2013.01);
(Continued)

(58) Field of Classification Search
None
See application file for complete search history.

(56) References Cited

U.S. PATENT DOCUMENTS

2010/0000292 A1*  1/2010  Karabacak .......... G01N 29/022
                                                         73/24.01
2010/0095750 A1   4/2010  Oita et al.
(Continued)

FOREIGN PATENT DOCUMENTS

CN    101617208 A    12/2009
CN    102507362 A    6/2012
(Continued)

OTHER PUBLICATIONS

Translated International Search Report for International Patent Application No. PCT/JP2019/030447, dated Oct. 21, 2019; 4 pages.
(Continued)

*Primary Examiner* — Brandi N Hopkins
*Assistant Examiner* — Nigel H Plumb
(74) *Attorney, Agent, or Firm* — Howard & Howard Attorneys PLLC

(57) ABSTRACT

A substance detection element is described herein. The substance detection element includes a supporting substrate, a plate-shaped beam, a detection electrode, and a substance adsorption film. The plate-shaped beam is provided with a piezoelectric element. The detection electrodes detects information about the vibration frequency of the beam. The substance adsorption films changes the vibration frequency of the beam by adhesion of a substance. The substance adsorption films and the detection electrodes are respectively provided at the same position on the front and the back of the beam.

15 Claims, 13 Drawing Sheets

(51) Int. Cl.
*G01N 29/24* (2006.01)
*G01N 33/00* (2006.01)
*H10N 30/30* (2023.01)

(52) U.S. Cl.
CPC ......... *H10N 30/302* (2023.02); *H10N 30/306* (2023.02); *G01N 2291/014* (2013.01); *G01N 2291/021* (2013.01)

(56) References Cited

U.S. PATENT DOCUMENTS

| | | | |
|---|---|---|---|
| 2010/0107736 | A1 | 5/2010 | Lu et al. |
| 2012/0270352 | A1* | 10/2012 | Huffman ................ H02N 1/002 257/E21.002 |
| 2014/0305191 | A1 | 10/2014 | Schmid et al. |
| 2018/0088088 | A1 | 3/2018 | Shimomai et al. |

FOREIGN PATENT DOCUMENTS

| | | |
|---|---|---|
| CN | 107870183 A | 4/2018 |
| JP | 2007-240252 A | 9/2007 |
| JP | 2009-204584 A | 9/2009 |
| JP | 2010-078334 A | 4/2010 |
| JP | 2010-117184 A | 5/2010 |
| JP | 2011-501158 A | 1/2011 |
| JP | 2011-179838 A | 9/2011 |
| JP | 2011-203007 A | 10/2011 |
| JP | 2012-2220454 A | 11/2012 |
| JP | 2012-242279 A | 12/2012 |
| JP | 2018-189584 A | 11/2018 |
| TW | 200714900 A | 4/2007 |

OTHER PUBLICATIONS

English language abstract and machine-assisted English language translation of Japanese Patent Publication No. JP 2018-189584 A extracted from www.espacenet.com database on Mar. 22, 2021; 12 pages.

English language abstract only of Japanese Patent Publication No. JP 2011/501158 A; see English language equivalent U.S. Patent Publication No. 2008/0163694 A1 extracted from www.espacenet.com database on Mar. 22, 2021; 1 page.

English language abstract and machine-assisted English language translation of Japanese Patent Publication No. JP 2010-117184 A extracted from www.espacenet.com database on Mar. 22, 2021; 17 pages.

English language abstract and machine-assisted English language translation of Japanese Patent Publication No. JP 2009-204584 A extracted from www.espacenet.com database on Mar. 22, 2021; 13 pages.

Chinese Office Action dated Nov. 17, 2023, issued for the corresponding CN patent application No. 201980063403.1.

\* cited by examiner

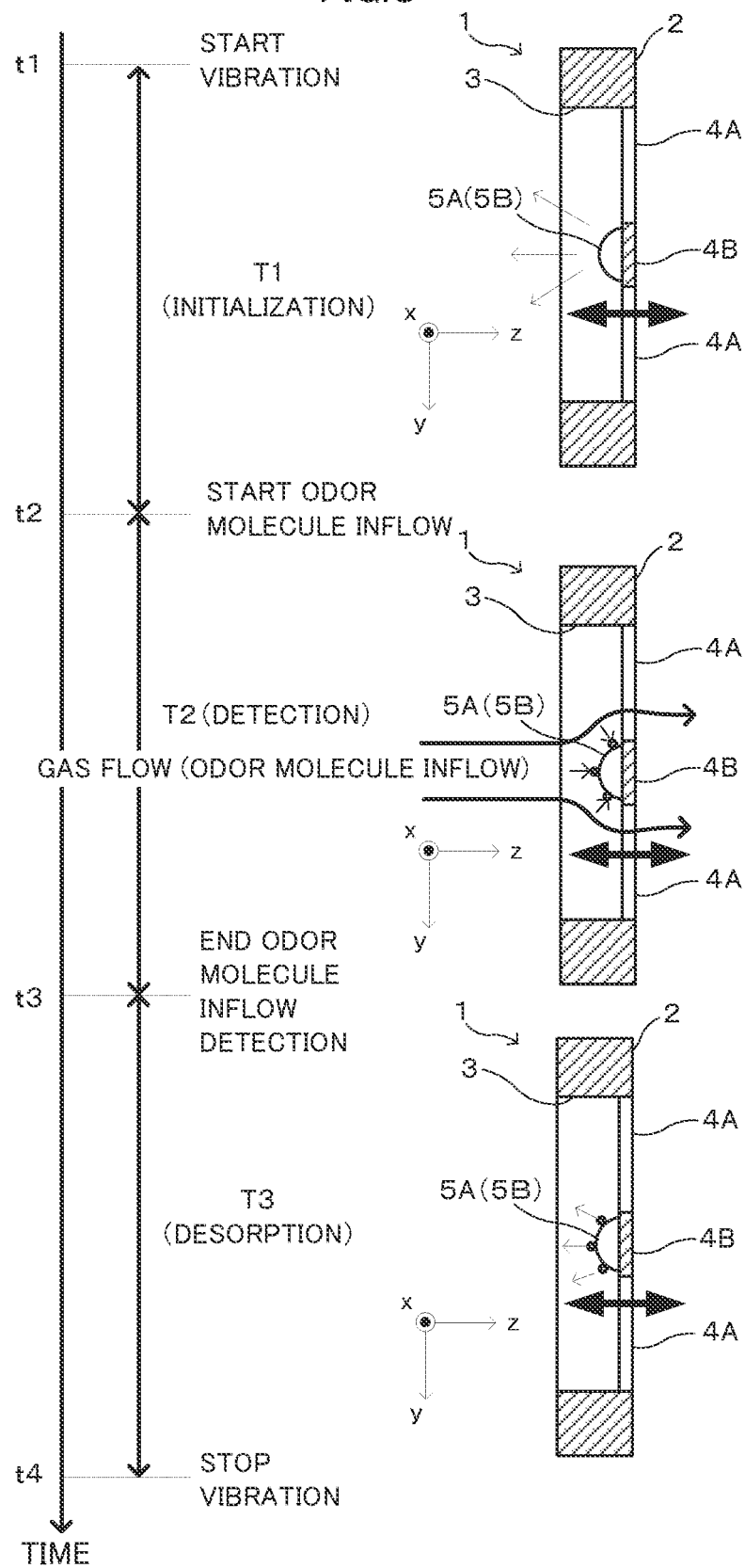

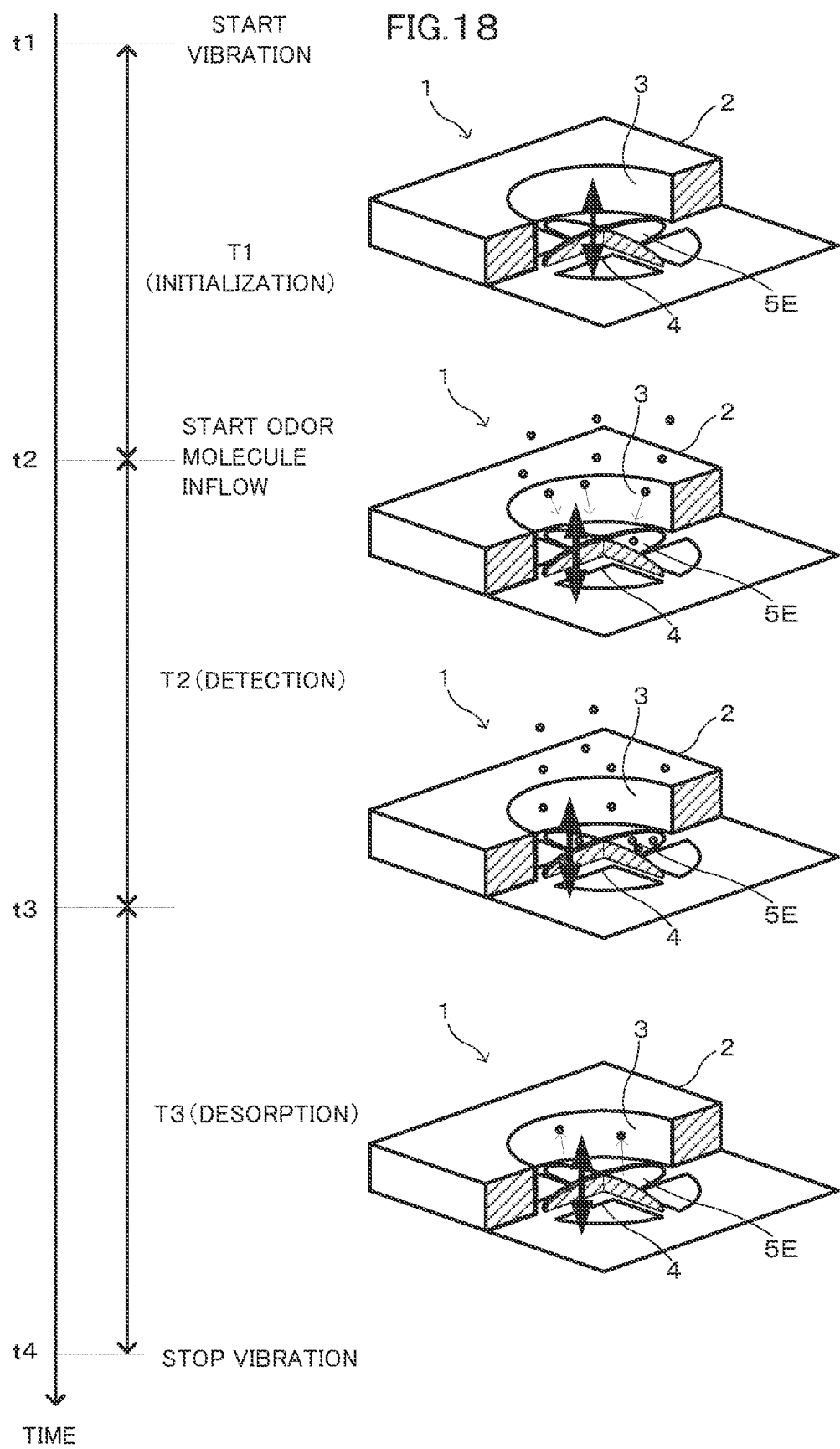

SUBSTANCE DETECTION DEVICE WITH IMPROVED EFFICIENCY

RELATED APPLICATIONS

This application is the National Stage Application of International Patent Application No. PCT/JP2019/030447, filed Aug. 2, 2019, which claims priority to and the benefit of Japanese Patent Nos. 2019-080654, filed on Apr. 22, 2019, and 2018-182353, filed on Sep. 27, 2018, the entire contents of which are hereby incorporated by reference.

TECHNICAL FIELD

The present disclosure relates to a substance detection element.

BACKGROUND ART

A chemical sensor device disclosed in Patent Literature 1 identifies a substance, based on a variation in a resonance frequency of an oscillator, the variation being caused when the substance adsorbs or desorbs. The chemical sensor device includes a plurality of oscillators indicating different substance adsorption-desorption characteristics, and each oscillator includes a piezoelectric substrate. When AC voltage is applied, the plurality of oscillators is excited by deformation of the piezoelectric substrates. Determination of an oscillator the resonance frequency of which is changed allows identification of a substance.

CITATION LIST

Patent Literature

Patent Literature 1: Unexamined Japanese Patent Application Publication No. 2009-204584.

SUMMARY OF INVENTION

Technical Problem

In the chemical sensor device disclosed in aforementioned Patent Literature 1, a plurality of oscillators is simply two-dimensionally arranged on a flat board, and the oscillators are not efficiently placed in such a way as to allow easy adsorption of a substance included in the air. With such a structure, the flat board itself may block a flow of an air current, and adsorption efficiency of a substance in each oscillator may decline.

The present disclosure has been made in view of the aforementioned actual circumstance, and an objective thereof is to provide a substance detection element that can more efficiently detect a substance.

Solution to Problem

In order to achieve the aforementioned objective, a substance detection element according to a first aspect of the present disclosure includes:
  a supporting substrate provided with a through hole;
  a plate-shaped beam extending from an edge of the through hole toward a facing edge in such a way as to cover part of the through hole and being provided with a piezoelectric element;
  a drive electrode vibrating the beam by applying voltage to the piezoelectric element;
  a detection electrode detecting information about a vibration frequency of the beam; and
  a substance adsorption film changing a vibration frequency of the beam by adhesion of a substance,
  wherein the substance adsorption film and the detection electrode are respectively provided at a same position on a front and a back of the beam.

In this case, the beam may be fixed to an edge of the through hole at at least two spots,
  a plurality of pairs of the substance adsorption film and the detection electrode respectively provided at a same position on a front and a back of the beam may be provided on the beam, and a substance adsorbed by the substance adsorption film may be different for the each pair.

The beam may be fixed to an edge of the through hole at both ends in a longitudinal direction of the beam, and
  pairs of the substance adsorption film and the detection electrode respectively provided at a same position on a front and a back of the beam may be provided on both sides viewed from a center of the beam.

The drive electrodes may be provided at both ends of the beam.

The drive electrode may be provided at a center of the beam.

The beam may include:
  a first beam fixed to an edge of the through hole at both ends in a longitudinal direction; and
  a second beam being fixed to an edge of the through hole at both ends in a longitudinal direction and intersecting the first beam.

Pairs of the substance adsorption film and the detection electrode respectively provided at a same position on a front and a back of the beam may be provided on both sides of the second beam viewed from a part where the first beam intersects the second beam.

Pairs of the substance adsorption film and the detection electrode respectively provided at a same position on a front and a back of the beam may be provided on both sides of the first beam viewed from a part where the first beam intersects the second beam.

The drive electrodes may be provided at both ends of the first beam.

The drive electrode may be provided in a part where the first beam intersects the second beam.

A width of the first beam may be set to be greater than a width of the second beam.

The first beam may be orthogonal to the second beam.

The drive electrode may desorb a substance adhering to the substance adsorption film by vibrating the beam.

The drive electrode may vibrate the beam in a film thickness direction of the substance adsorption film.

A substance detection element according to a second aspect of the present disclosure includes:
  a supporting substrate;
  a plate-shaped beam provided with a piezoelectric element, at least one end of the beam being supported by the supporting substrate;
  a drive electrode vibrating the beam by applying voltage to the piezoelectric element; and
  a substance adsorption film being provided on the beam and changing a vibration frequency of the beam by adhesion of a substance,
  wherein the drive electrode desorbs a substance adhering to the substance adsorption film by vibrating the beam.

The drive electrode may vibrate the beam in a film thickness direction of the substance adsorption film.

Advantageous Effects of Invention

According to the present disclosure, a substance adsorption film changing the vibration frequency of a beam by adhesion of a substance and a detection electrode detecting information about the vibration frequency of the beam are respectively provided at the same position on the front and the back of the beam. Information about the vibration frequency of the beam can be thereby detected with high sensitivity at a position where a change in the vibration frequency of the beam due to adhesion of a substance to the substance adsorption film is significant, and therefore the substance can be more efficiently detected.

BRIEF DESCRIPTION OF DRAWINGS

FIG. 9 is a diagram illustrating a chemical substance detection operation using the substance detection element;

FIG. 18 is a diagram illustrating a chemical substance detection operation using another substance detection element.

DESCRIPTION OF EMBODIMENTS

An embodiment of the present disclosure will be described in detail below. A substance detection element according to the present embodiment is manufactured by use of micro-electro-mechanical systems (MEMS) being a semiconductor manufacturing technology for achieving micromachining.

Figure 1:
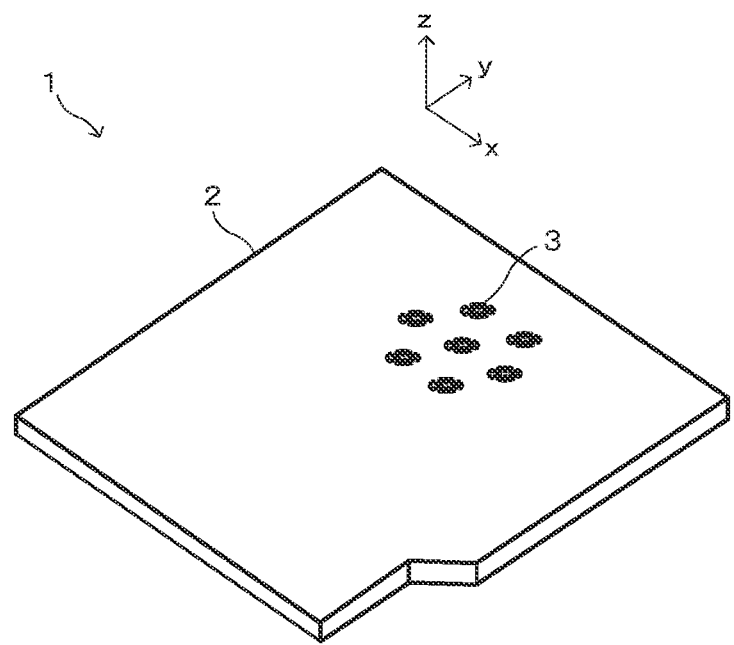
FIG. 1 is a perspective view of a substance detection element according to Embodiment 1 of the present disclosure.

As illustrated in FIG. 1, a substance detection element 1 according to the present embodiment includes an almost rectangular flat-plate-shaped supporting substrate 2. For example, the supporting substrate 2 is manufactured from a silicon on insulator (SOI) substrate. An SOI substrate is a semiconductor substrate having a laminated structure including a BOX layer being a buried oxide film and a silicon (SOI) layer being a semiconductor layer on the BOX layer and is a wafer containing an oxide film.

Figure 2:
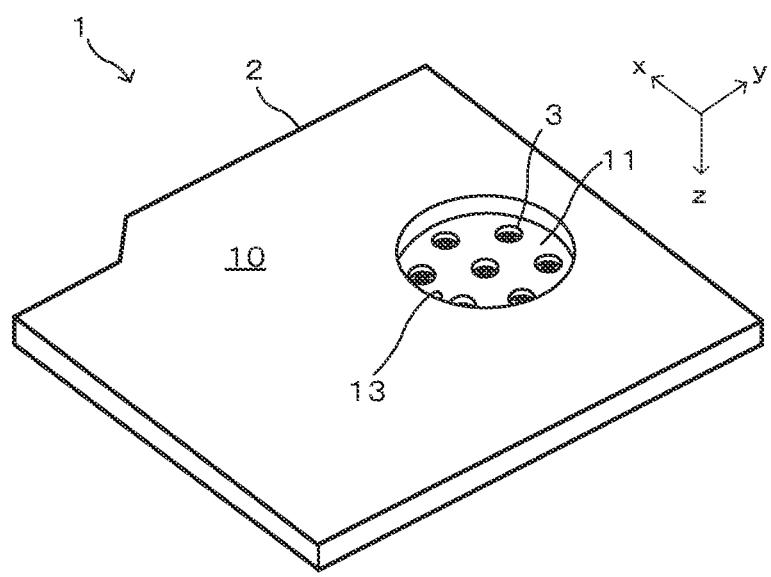
FIG. 2 is a perspective view of the substance detection element in FIG. 1 viewed from the opposite side.

The supporting substrate 2 is formed by a Si supporting layer 11 being laminated on a base 10 made up of resin, the Si supporting layer 11 being made up of the BOX layer formed of a substrate wafer and the buried oxide film, as illustrated in FIG. 2. A Si active layer 12 (see FIG. 5A and FIG. 5B) being an element wafer active layer is laminated on the Si supporting layer 11.

Part of the base 10 of the supporting substrate 2 is provided with a circular opening 13, and the Si supporting layer 11 is exposed in the opening 13 part. The Si supporting layer 11 and the Si active layer 12 in the opening 13 part are provided with seven through holes 3. The through holes 3 are circular and have the same diameter.

Figure 3:
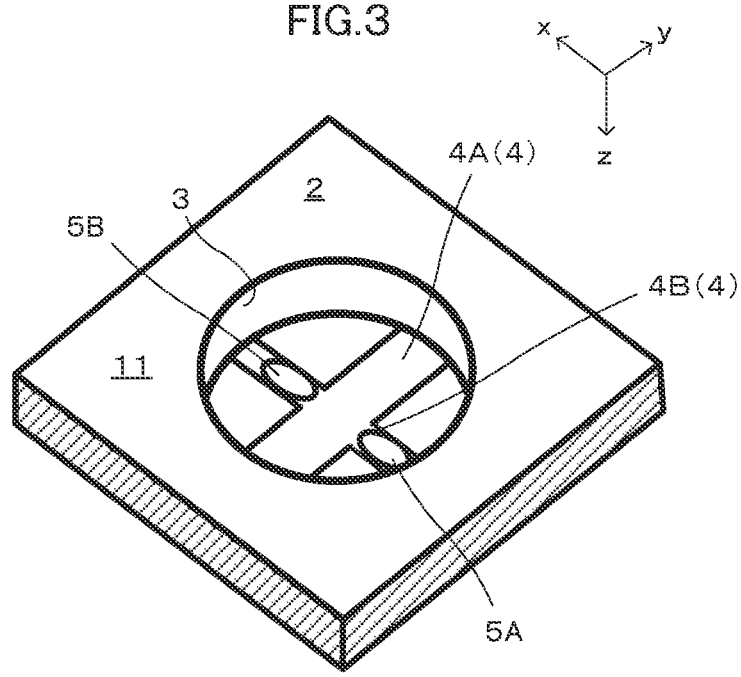
FIG. 3 is a first enlarged perspective view illustrating a partially broken up vicinity of a through hole.
Figure 4:
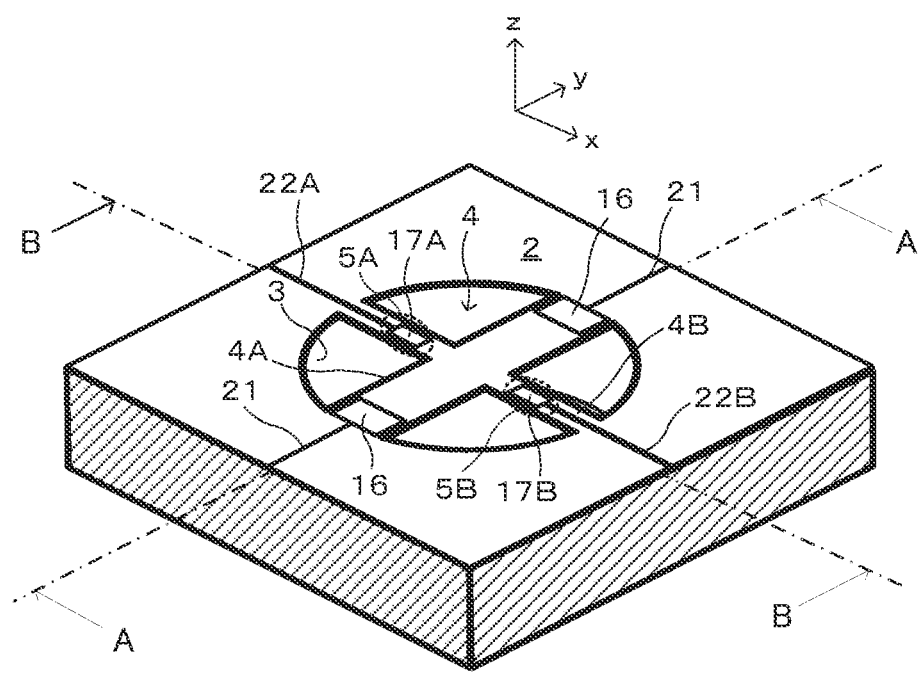
FIG. 4 is a second enlarged perspective view illustrating a partially broken up vicinity of the through hole.

Each of the through holes 3 is provided with a plate-shaped beam 4, as illustrated in FIG. 3 and FIG. 4. The beam 4 according to the present embodiment includes a long and narrow plate-shaped first beam 4A and a long and narrow plate-shaped second beam 4B. The beam 4 (the first beam 4A and the second beam 4B) includes parts each extending from an edge of the through hole 3 formed by the Si active layer 12 toward a facing edge.

Each of the first beam 4A and the second beam 4B is fixed to an edge of a through hole 3 at both ends in a longitudinal direction of the beam. The first beam 4A and the second beam 4B intersect (are orthogonal to) each other and connect at the center. The width of the first beam 4A is greater than the width of the second beam 4B, according to the present embodiment. The widths respectively indicate the length of the first beam 4A in a transverse direction and the length of the second beam 4B in the transverse direction. The beam 4 does not cover the entire through hole 3 but covers part of the through hole 3. Accordingly, the beam 4 prevents gas from staying in the through hole 3 and facilitates the gas to pass through the through hole 3.

As illustrated in FIG. 3, the beam 4 (second beam 4B) supports substance adsorption films 5A and 5B adsorbing substances being detection targets. The substance adsorption films 5A and 5B are respectively placed at separate locations on the second beam 4B. Each of the substance adsorption films 5A and 5B has a long and narrow hemispherical shape or a cup shape having a raised outer periphery and a concave center and thereby allows increase in a surface area exposed to gas. Each of the substance adsorption films 5A and 5B can thereby easily adsorb a substance being included in gas (such as air) and being a detection target. The substance adsorption films 5A and 5B are mounted on the beam 4 in an attachable and detachable manner and are exchangeable for other substance adsorption films.

The substance adsorption films 5A and 5B adsorb different substances. For example, a substance being a detection target is a gaseous substance constituting a chemical substance being included in the air and being a detection target (hereinafter referred to as a "constituent substance") in an odor-constituting chemical substance group (odor factors). For example, chemical substances being detection targets include odor-causing substances having peculiar odor such as ammonia, mercaptan, aldehyde, hydrogen sulfide, and amine. When a certain time elapses after adsorption of a constituent substance constituting an odor-causing substance, the adsorbed constituent substance separates, and therefore the substance adsorption films 5A and 5B are reusable.

The beam 4 is formed to change a vibration frequency (such as a resonance frequency) by adsorption of constituent substances to the substance adsorption films 5A and 5B. The substance adsorption films 5A and 5B are placed at a through hole 3 being a pass-through opening of gas including a constituent substance, and therefore it is easy for the substance adsorption films 5A and 5B to adsorb the constituent substance included in the gas. In order for vibration of the beam 4 not to be affected by vibration of a device into which the substance detection element 1 is built, it is desirable that the vibration frequency of the beam 4 be set higher than the vibration frequency of the device in order that the two are different.

Drive electrodes 16 are formed at both ends of the first beam 4A, as illustrated in FIG. 4. Further, detection electrodes 17A and 17B are formed on the second beam 4B. Drive signal lines 21 and detection signal lines 22A and 22B as conducting wires are formed on the supporting substrate 2. The drive signal lines 21 are connected to the drive electrodes 16. The detection signal line 22A is connected to the detection electrode 17A, and the detection signal line 22B is connected to the detection electrode 17B. Voltage signals driving the beam 4 are applied to the drive electrodes 16 through the drive signal lines 21. Further, a voltage signal from the detection electrode 17A is output through the detection signal line 22A, and a voltage signal from the detection electrode 17B is output through the detection signal line 22B.

The substance adsorption film 5A and the detection electrode 17A are respectively provided at the same position on the front and the back of the beam 4 (second beam 4B). The substance adsorption film 5B and the detection electrode 17B are respectively provided at the same position on the front and the back of the beam 4 (second beam 4B).

In other words, according to the present embodiment, the beam 4 is fixed to the edge of the through hole 3 at at least two spots, and a pair of the substance adsorption film 5A and the detection electrode 17A respectively provided at the same position on the front and the back of the beam 4, and a pair of the substance adsorption film 5B and the detection electrode 17B respectively provided at the same position on the front and the back of the beam 4 are provided on the beam 4.

More specifically, the second beam 4B is fixed to the edge of a through hole 3 at both ends in the longitudinal direction of the second beam 4B. The pair of the substance adsorption film 5A and the detection electrode 17A respectively provided at the same position on the front and the back of the second beam 4B, and the pair of the substance adsorption film 5B and the detection electrode 17B respectively provided at the same position on the front and the back of the second beam 4B are provided on both sides in an x-axis direction viewed from the center of the second beam 4B. Furthermore, the pair of the substance adsorption film 5A and the detection electrode 17A respectively provided at the same position on the front and the back of the beam 4, and the pair of the substance adsorption film 5B and the detection electrode 17B respectively provided at the same position on the front and the back of the beam 4 are provided on both sides of the second beam 4B viewed from a part where the first beam 4A intersects the second beam 4B.

Figure 5A:
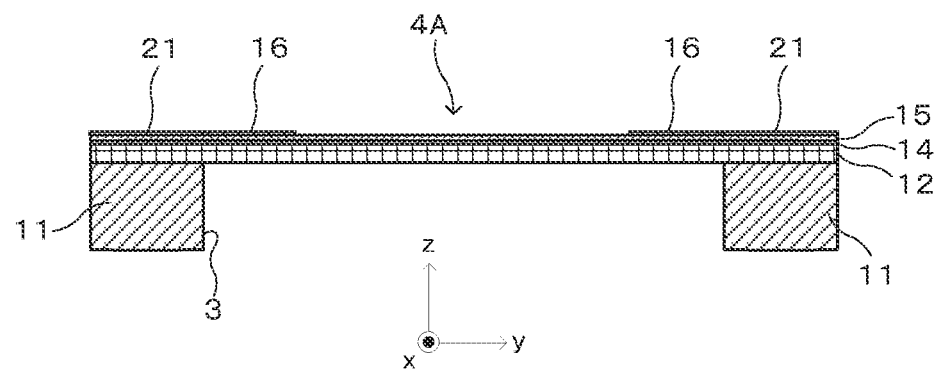
FIG. 5A is a cross-sectional view taken along a line A-A in FIG. 4.

As illustrated in FIG. 5A being a cross-sectional view taken along a line A-A in FIG. 4, the first beam 4A is mainly formed by the Si active layer 12 of the supporting substrate 2. A lower electrode layer 14 is formed on the Si active layer 12, and a piezoelectric element 15 is formed on the lower electrode layer 14. The drive electrodes 16 are formed at the edge of a through hole 3 of the second beam 4B in such a way as to be in contact with the piezoelectric element 15. The lower electrode layer 14, the piezoelectric element 15, and the drive electrode 16 form a piezoelectric layer.

Figure 5B:
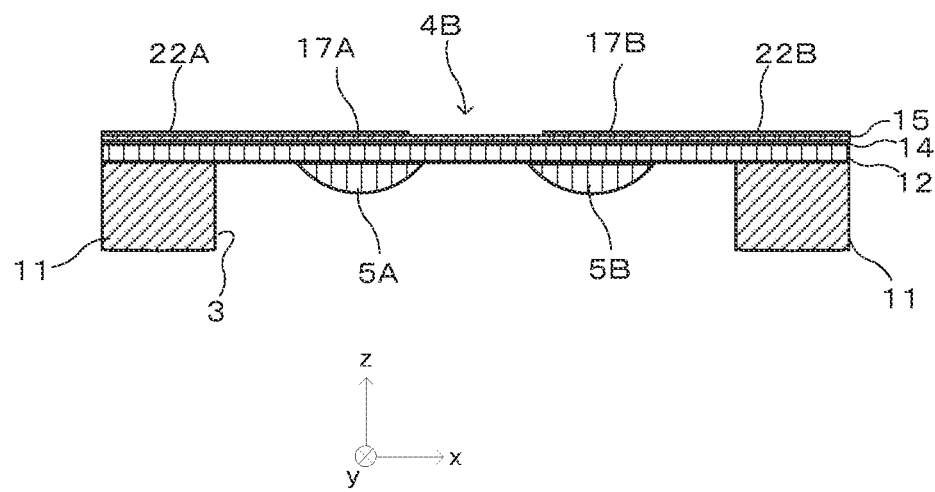
FIG. 5B is a cross-sectional view taken along a line B-B in FIG. 4.

On the other hand, as illustrated in FIG. 5B being a cross-sectional view taken along a line B-B in FIG. 4, the second beam 4B is mainly formed by the Si active layer 12 of the supporting substrate 2. The lower electrode layer 14 is formed on the Si active layer 12, and the piezoelectric element 15 is formed on the lower electrode layer 14. The detection electrodes 17A and 17B are formed at the edge of the through hole 3 of the second beam 4B in such a way as to be in contact with the piezoelectric element 15. The lower electrode layer 14, the piezoelectric element 15, and the detection electrodes 17A and 17B form the piezoelectric layer.

The lower electrode layer 14 is formed of an electroconductive material (such as metal such as aluminum or copper). The same holds for the drive electrodes 16 and the detection electrodes 17A and 17B. For example, the piezoelectric element 15 is formed of a material such as lead zirconate titanate (PZT) (a material exhibiting a piezoelectric characteristic). The piezoelectric element 15 has a property of extending and contracting in a longitudinal direction (a direction orthogonal to a thickness direction) when voltage of predetermined polarity is applied in the thickness direction. Illustration of the BOX layer is omitted in FIG. 5A and FIG. 5B.

Figure 6:
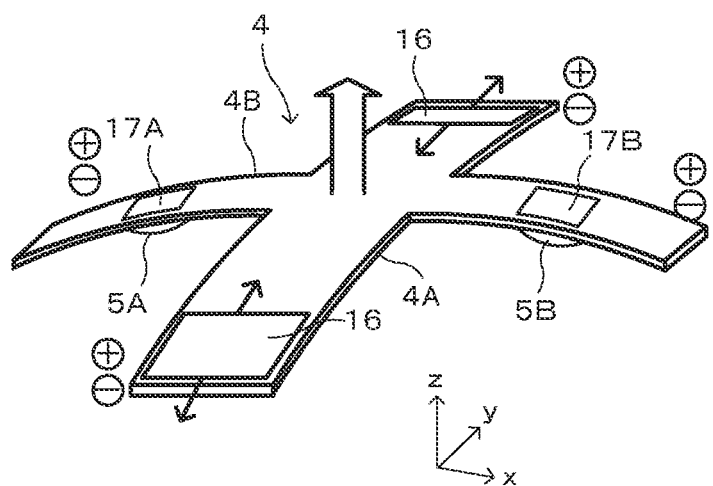
FIG. 6 is a first diagram illustrating a state of deformation of a beam.

When voltage of polarity causing the drive electrodes 16 to be positive and causing the lower electrode layer 14 to be negative (hereinafter referred to as positive polarity) is applied, the piezoelectric layer extends in the longitudinal direction, and therefore the first beam 4A is warped to be upwardly convex (in a +z-direction), and the second beam 4B is accordingly warped to be upwardly convex (in the +z-direction), as illustrated in FIG. 6. Consequently, voltage of polarity causing the detection electrodes 17A and 17B to be positive and causing the lower electrode layer 14 to be negative (hereinafter referred to as positive polarity) is generated.

Figure 7:
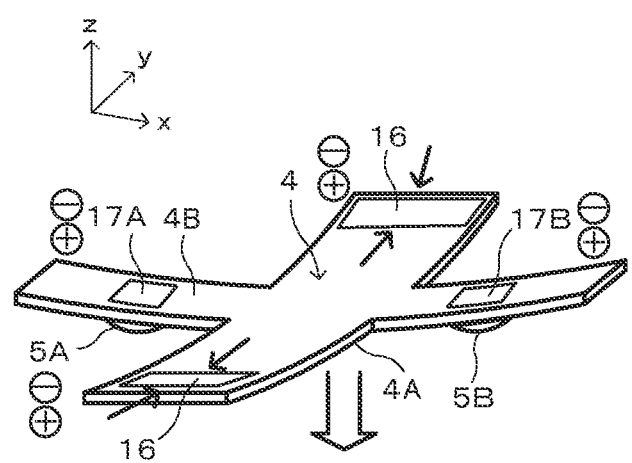
FIG. 7 is a second diagram illustrating a state of deformation of the beam.

On the other hand, when voltage of polarity causing the drive electrodes 16 to be negative and causing the lower electrode layer 14 to be positive (hereinafter referred to as negative polarity) is applied, the piezoelectric layer of the first beam 4A contracts in the longitudinal direction, and therefore the first beam 4A is warped to be downwardly convex (in a −z-direction), and the second beam 4B is accordingly warped to be downwardly convex (in the −z-direction), as illustrated in FIG. 7. Consequently, voltage of polarity causing the detection electrodes 17A and 17B to be negative and causing the lower electrode layer 14 to be positive (hereinafter referred to as negative polarity) is generated.

Naturally, a piezoelectric element having a property of contracting in the longitudinal direction when voltage causing the drive electrode 16 side to be positive and causing the lower electrode layer 14 side to be negative is applied between both electrodes and extending in the longitudinal direction when voltage causing the drive electrode 16 side to be negative and causing the lower electrode layer 14 side to be positive is applied between both electrodes may be used. In this case, when positive-polarity voltage is applied, the piezoelectric element is warped to be downwardly convex, and positive-polarity voltage is generated at the detection electrodes 17A and 17B. On the other hand, when negative-polarity voltage is applied, the piezoelectric element is warped to be upwardly convex, and negative-polarity voltage is generated at the detection electrodes 17A and 17B. Thus, the first beam 4A has only to bend and vibrate by extension and contraction of the piezoelectric layer, and the second beam 4B has only to cause the piezoelectric layer to extend and contract by bending and generate voltage.

In any event, the deformation illustrated in FIG. 6 or FIG. 7 can be generated by applying voltage of predetermined polarity between the drive electrodes 16 and the lower electrode layer 14 (see FIG. 5A). A degree of deformation depends on an applied voltage value. When the deformation illustrated in FIG. 6 or FIG. 7 is generated, voltage of predetermined polarity can be generated between the detection electrodes 17A and 17B and the lower electrode layer 14. Magnitude of the voltage depends on the second beam 4B. A polarizing action changes with the material constituting the piezoelectric element (such as a bulk or a thin film), and therefore a relation between extension and contraction, and polarity of voltage may become opposite to the above description.

For example, when sinusoidally changing voltage is applied between the drive electrodes 16 and the lower electrode layer 14, the first beam 4A vibrates sinusoidally. The second beam 4B also vibrates according to the vibration of the first beam 4A. In other words, the drive electrodes 16 vibrate the beam 4 by applying voltage to the piezoelectric element 15. When the second beam 4B vibrates, a sinusoidally changing potential difference is generated between the detection electrodes 17A and 17B and the lower electrode layer 14. The detection electrodes 17A and 17B detect information about the vibration frequency of the beam 4.

Furthermore, when the frequency of the sinusoidal voltage applied between the drive electrodes 16 and the lower electrode layer 14 is increased or decreased, the frequency of the vibration of the first beam 4A and the second beam 4B also increases or decreases, and the frequencies of the voltage signals generated between the detection electrodes 17A and 17B and the lower electrode layer 14 also increase or decrease. As the frequency of the vibration of the first beam 4A and the second beam 4B approaches the resonance frequency of the beam 4, the vibration amplitude of the beam 4 increases, and when the frequency reaches the resonance frequency of the beam 4, the vibration amplitude of the beam 4 is maximized.

As described above, the beam 4 is formed to change the vibration frequency (such as the resonance frequency) by adsorption of a constituent substance to the substance adsorption films 5A and 5B. Further, the vibration frequency of the beam 4 changes according to a degree of adsorption of the constituent substance to the substance adsorption films 5A and 5B. A frequency maximizing the vibration amplitude of the beam 4 thereby changes. Conversely, a change from a state in which a constituent substance is not adsorbed to the substance adsorption films 5A and 5B to a state in which the constituent substance is adsorbed can be detected by determining a change in the vibration frequency maximizing the amplitude of the voltage signal between the detection electrodes 17A and 17B and the lower electrode layer 14.

The potential difference generated between the detection electrode 17A and the lower electrode layer 14 turns to a voltage signal and is output through the detection signal line 22A. The potential difference generated between the detection electrode 17B and the lower electrode layer 14 turns to a voltage signal and is output through the detection signal line 22B. By determining the output voltage signals as information about the vibration frequency of the beam 4 and detecting a change in the vibration frequency of the beam 4, based on the information, inclusion of a substance adsorbed by the substance adsorption film 5A or 5B in gas passing through the through hole 3 can be detected.

Figure 8:
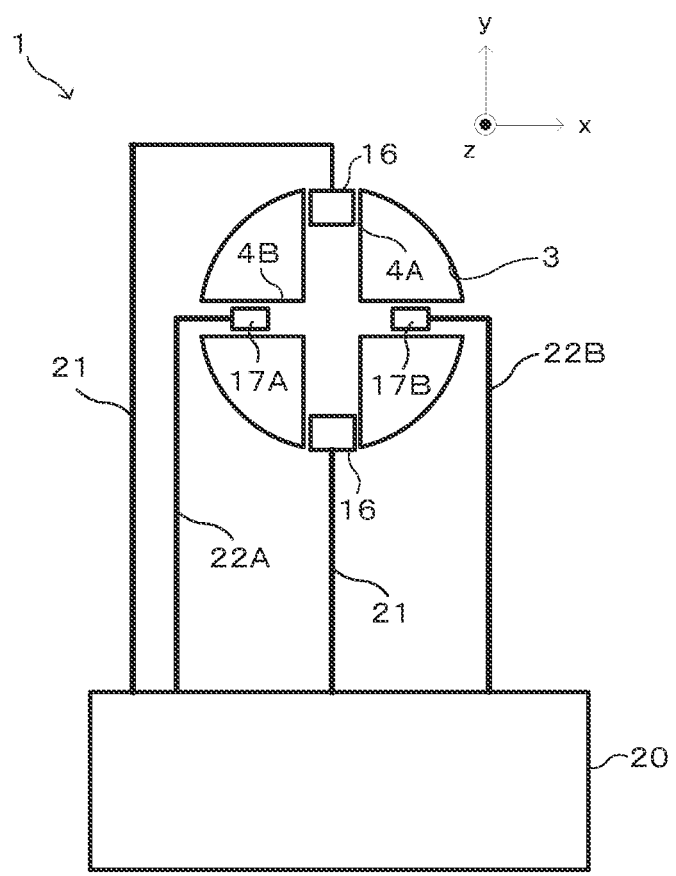
FIG. 8 is a plan view illustrating wiring in the substance detection element.

As illustrated in FIG. 8, a signal processing circuit 20 is provided in the substance detection element 1. The signal processing circuit 20 is connected to the two drive signal lines 21 and the two detection signal lines 22A and 22B. The two drive signal lines 21 output from the signal processing circuit 20 are connected to the pair of the drive electrodes 16. The two detection signal lines 22A and 22B respectively output from the detection electrodes 17A and 17B are independently connected to the signal processing circuit 20. The signal processing circuit 20 inputs and outputs various voltage signals based on the potential of the lower electrode layer 14 (see FIG. 5A and FIG. 5B).

The signal processing circuit 20 outputs, for example, sinusoidal voltage signals to the drive electrodes 16 relating to each through hole 3 through the drive signal lines 21 and inputs voltage signals output from the detection electrodes 17A and 17B relating to each through hole 3 through the detection signal lines 22A and 22B. The signal processing circuit 20 detects a change in the vibration frequency (such as the resonance frequency) of the beam 4, based on the input voltage signals. For example, the substance detection element 1 can detect adsorption of a constituent substance in units of nanograms (ng).

In the substance detection element 1, the beam 4 is provided for each through hole 3, and types of the substance adsorption films 5A and 5B supported by each beam 4 are different. The signal processing circuit 20 inputs voltage signals output from the detection electrodes 17A and 17B at the through hole 3 through the detection signal lines 22A and 22B and detects a change in the vibration frequency of the beam 4, that is, adsorption of a constituent substance to the substance adsorption film 5A or 5B relating to the beam 4, based on the input voltage signal. The detection electrode 17A is provided on the back of the substance adsorption film 5A, and therefore when a substance adheres to the substance adsorption film 5A, a change in the vibration frequency of the beam 4 is detected, based on the voltage signal connected by the detection electrode 17A. The detection electrode 17B is provided on the back of the substance adsorption film 5B, and therefore when a substance adheres to the substance adsorption film 5B, a change in the vibration frequency of the beam 4 is detected, based on the voltage signal connected by the detection electrode 17B. The signal processing circuit 20 includes a memory and stores a detection result of a constituent substance for each of the substance adsorption films 5A and 5B into the memory.

Next, a chemical substance detection operation by the substance detection element 1 according to the present embodiment will be described. As illustrated in FIG. 8, the signal processing circuit 20 starts outputting sinusoidal voltage signals at any frequency to the drive electrodes 16. Vibration of the beam 4 is thereby started at a point t1, as illustrated in FIG. 9. Constituent substances adsorbing to the substance adsorption films 5A and 5B before measurement are desorbed by the vibration, and the substance adsorption films 5A and 5B are initialized. A period from the point t1 to a point t2 is determined to be an initialization period T1 for initializing the substance adsorption film 5A.

The signal processing circuit 20 continues the vibration of the beam 4 past the point t2. In a period T2 from the point t2 to a point t3, detection of a chemical substance is performed. In order to detect various chemical substances included in gas, the substance detection element 1 is placed in a flow of gas at the point t2. Detection of a constituent substance constituting a chemical substance included in the gas passing through a through hole 3 is thereby started. The beam 4 supporting the substance adsorption films 5A and 5B adsorbing constituent substances does not cover the entire through hole 3 but covers part of the through hole 3. Therefore, the beam 4 prevents the gas including a chemical substance being a detection target from staying in the through hole 3 and facilitates passing of the gas through the through hole 3.

In the period T2, the signal processing circuit 20 inputs voltage signals output from the detection electrodes 17A and 17B at the through hole 3 through the detection signal lines 22A and 22B and detects a change in the vibration frequency of the beam 4, that is, adsorption of a constituent substance to the substance adsorption film 5A or 5B relating to the beam 4, based on the input voltage signals.

At the point t3, the substance detection element 1 is removed from the flow of the gas. The detection of the chemical substance thereby ends. However, in a period T3 from the point t3 to a point t4, the signal processing circuit 20 continues the vibration of the beam 4. The constituent substance thereby desorbs from the substance adsorption film 5A or 5B. At the point t4, the processing by the substance detection element 1 ends.

When detection of a chemical substance is performed again, the operations in the periods T1 to T3 are repeated.

According to the present embodiment, the substance adsorption films 5A and 5B are provided on the beam 4 through which gas including a chemical substance passes, and the gas including the chemical substance being a detection target can easily pass in the vicinity of the substance adsorption films 5A and 5B; and therefore the chemical substance can be more efficiently detected.

As described in detail above, according to the present embodiment, the substance adsorption films 5A and 5B changing the vibration frequency of the beam 4 by adhesion of a substance and the detection electrodes 17A and 17B detecting information about the vibration frequency of the beam 4 are respectively provided at the same positions on the front and the back of the beam 4. The information about the vibration frequency of the beams 4 can be thereby detected with high sensitivity at a position where a change in the vibration frequency of the beam 4 due to adhesion of the substance to the substance adsorption film 5A or 5B is significant, and therefore the substance can be more efficiently detected.

Further, according to the present embodiment, two types of substances can be detected for each through hole, and therefore a size of a device capable of detecting the same types of substances can be reduced. Conversely, types of detectable substances can be increased keeping the same device size.

The positions of the substance adsorption films 5A and 5B may deviate from the positions of the detection electrodes 17A and 17B, respectively, to some extent. The amount of deviation has only to be negligibly less than the distance between the substance adsorption films and the distance between the detection electrodes. Further, three or more pairs of the substance adsorption film and the detection electrode may be placed on the same beam as long as each of the distance between the substance adsorption films and the distance between the detection electrodes is equal to or greater than a distance allowing separate detection of a change in the vibration frequency.

Further, according to the present embodiment, the width of the first beam 4A on which the drive electrodes 16 are provided is greater than the width of the second beam 4B on which detection electrodes 17A and 17B are provided. Thus, a level of a detected voltage signal can be increased by increasing an amount of displacement of the beam 4.

According to the present embodiment, the width of the first beam 4A is set to be greater than the width of the second beam 4B. However, the present disclosure is not limited to the above. The width (the length in the transverse direction) of the first beam 4A and the width (the length in the transverse direction) of the second beam 4B may be the same. Further, the length of the first beam 4A may be shortened by decreasing the diameter of a through hole 3. Thus, an effect of external vibration can be reduced by setting a higher vibration frequency of the entire beam 4, and in addition, detection precision of adsorption of a constituent substance can be improved by increasing a variation of the vibration frequency of the beam 4 per unit weight of an adsorbing constituent substance.

It is desirable to determine the width and the length of the beam 4 in relation to the size of a through hole 3 required for a flow of gas.

Further, according to the present embodiment, the beam 4 is fixed to the edge of the through hole 3 at at least two spots. Thus, compared with a cantilever beam 4, the beam 4 can be more stably held, and the vibration frequency of the beam 4 can be increased.

Figure 10A:
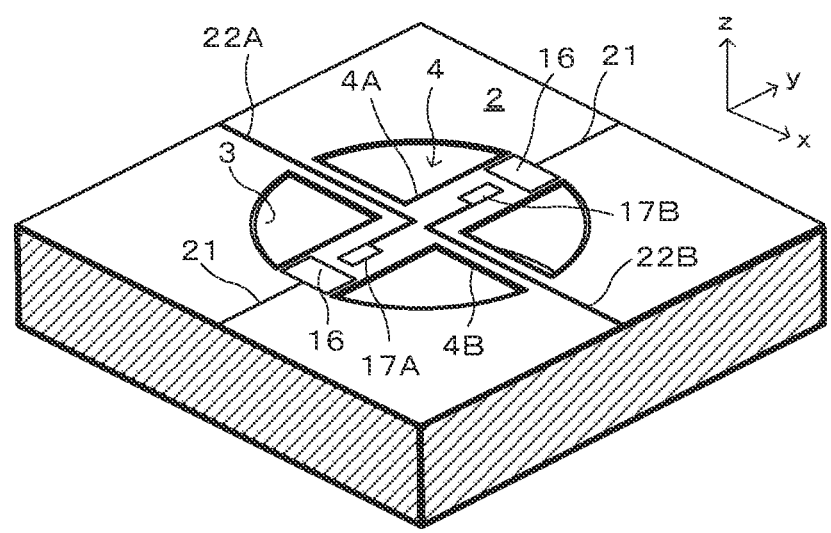
FIG. 10A is a perspective view (front) illustrating a first modified example of the substance detection element.
Figure 10B:
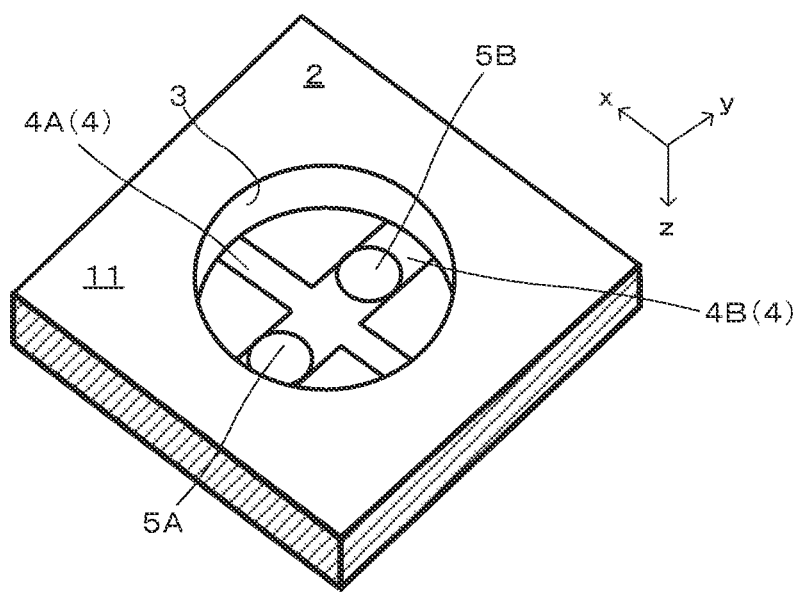
FIG. 10B is a perspective view (back) illustrating the first modified example of the substance detection element.

Placement of the drive electrodes 16, the detection electrodes 17A and 17B and the substance adsorption films 5A and 5B on the beam 4 is not limited to that according to the present embodiment. For example, the pair of the substance adsorption film 5A and the detection electrode 17A, and the pair of the substance adsorption film 5B and the detection electrode 17B may be provided on the first beam 4A instead of the second beam 4B, as illustrated in FIG. 10A and FIG. 10B. Specifically, the pair of the substance adsorption film 5A and the detection electrode 17A respectively provided at the same position on the front and the back of the beam 4, and the pair of the substance adsorption film 5B and the detection electrode 17B respectively provided at the same position on the front and the back of the beam 4 are provided on both sides of the first beam 4A viewed from a part where the first beam 4A intersects the second beam 4B.

Figure 11A:
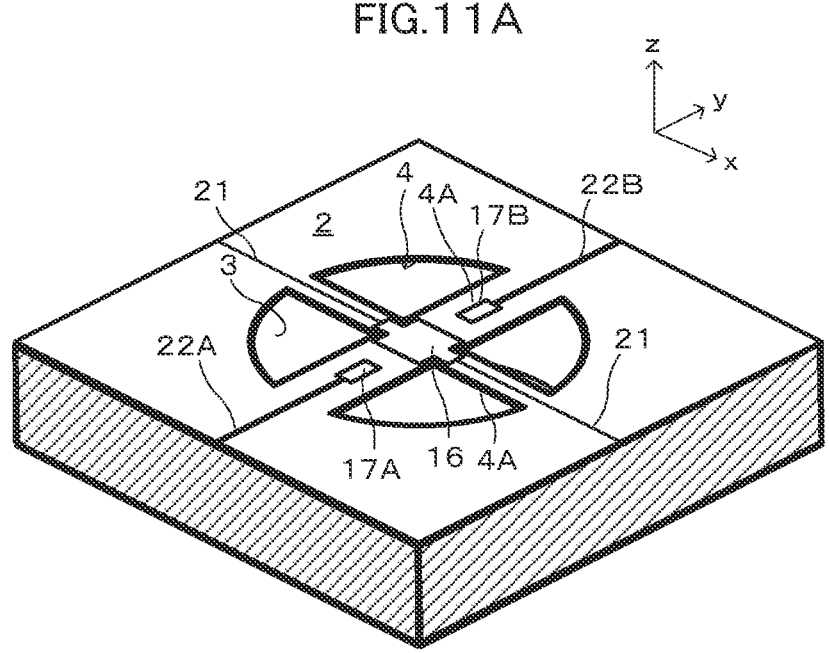
FIG. 11A is a perspective view (front) illustrating a second modified example of the substance detection element.
Figure 11B:
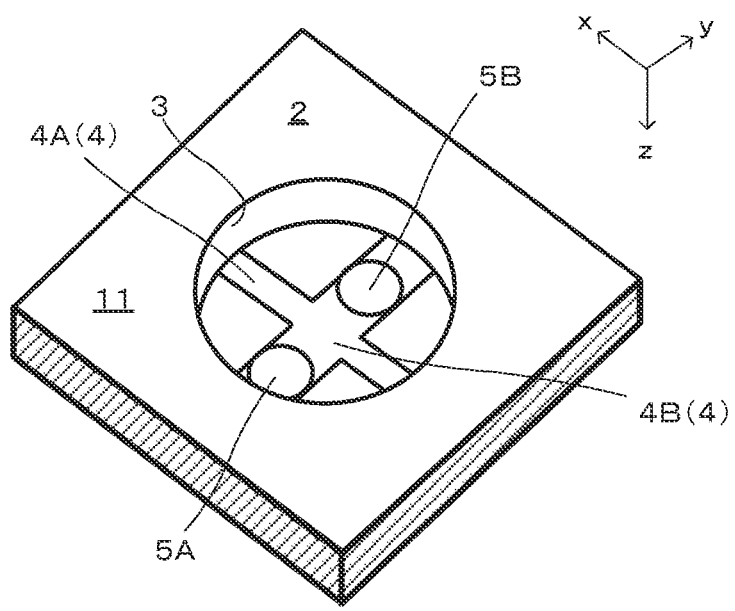
FIG. 11B is a perspective view (back) illustrating the second modified example of the substance detection element.

Only one drive electrode 16 may be provided at the center of the first beam 4A and the second beam 4B, as illustrated in FIG. 11A and FIG. 11B. Specifically, the drive electrode 16 may be provided in a part where the first beam 4A intersects the second beam 4B. The first beam 4A and the second beam 4B can be vibrated by applying a voltage signal to the drive electrode 16.

Figure 12A:
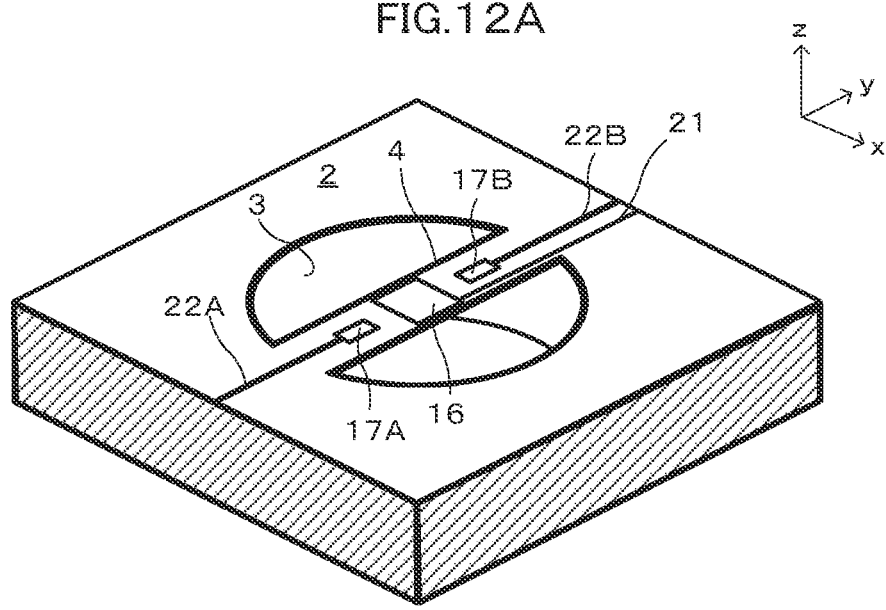
FIG. 12A is a perspective view (front) illustrating a third modified example of the substance detection element.
Figure 12B:
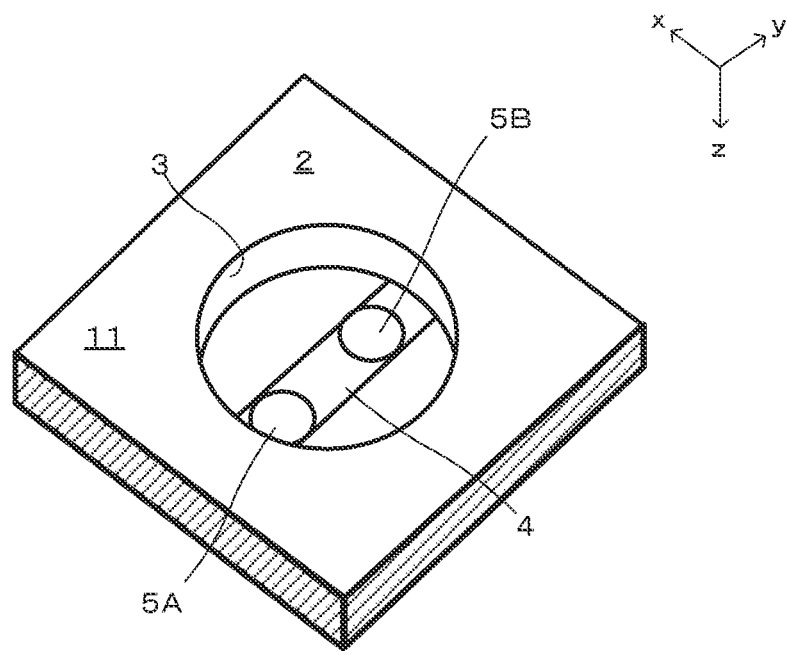
FIG. 12B is a perspective view (back) illustrating the third modified example of the substance detection element.

Further, the beam 4 may be extending in only one direction and be fixed at the edge of a through hole 3 at both ends in the longitudinal direction, as illustrated in FIG. 12A and FIG. 12B. In this case, the drive electrode 16 may be provided at the center of the beam 4, and the pair of the substance adsorption film 5A and detection electrode 17A respectively provided at the same position on the front and the back of the beam 4, and the pair of the substance adsorption film 5B and the detection electrode 17B respectively provided at the same position on the front and the back of the beam 4 may be provided on both sides viewed from the center of the beam 4.

Figure 13A:
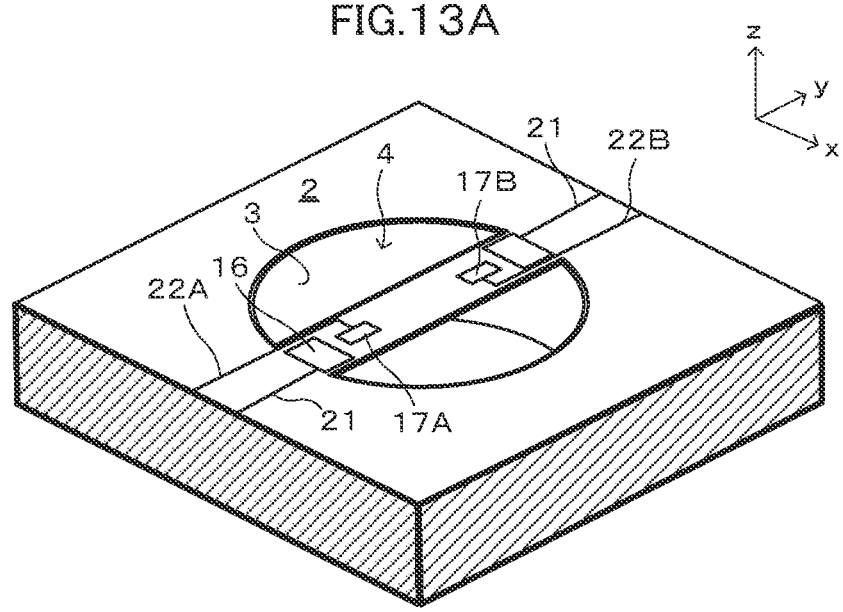
FIG. 13A is a perspective view (front) illustrating a fourth modified example of the substance detection element.
Figure 13B:
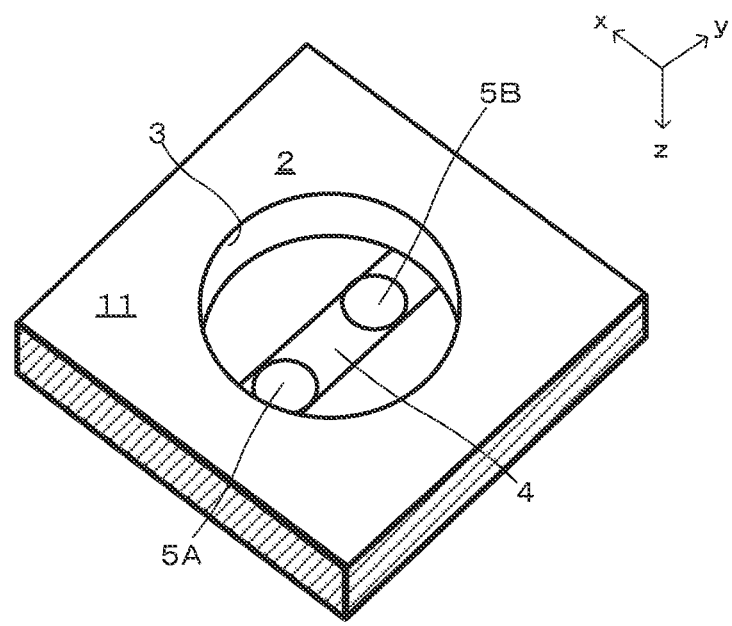
FIG. 13B is a perspective view (back) illustrating the fourth modified example of the substance detection element.

Further, when the beam 4 is extending in only one direction and is fixed to the edge of a through hole 3 at both ends in the longitudinal direction, drive electrodes 16 may be provided at both ends of the beam 4, as illustrated in FIG. 13A and FIG. 13B. Further, the pair of the substance adsorption film 5A and the detection electrode 17A respectively provided at the same position on the front and the back of the beam 4, and the pair of the substance adsorption film 5B and the detection electrode 17B respectively provided at the same position on the front and the back of the beam 4 may be provided on both sides viewed from the center of the beam 4.

In the description above, the level of voltage output from the detection electrodes 17A and 17B is maximized in the placement illustrated in FIG. 11A and FIG. 11B. In other words, the voltage level is maximized when the drive electrode 16 is mounted at the center of the beam 4, and the detection electrodes 17A and 17B are placed on the first beam 4A with a large width.

Figure 14A:
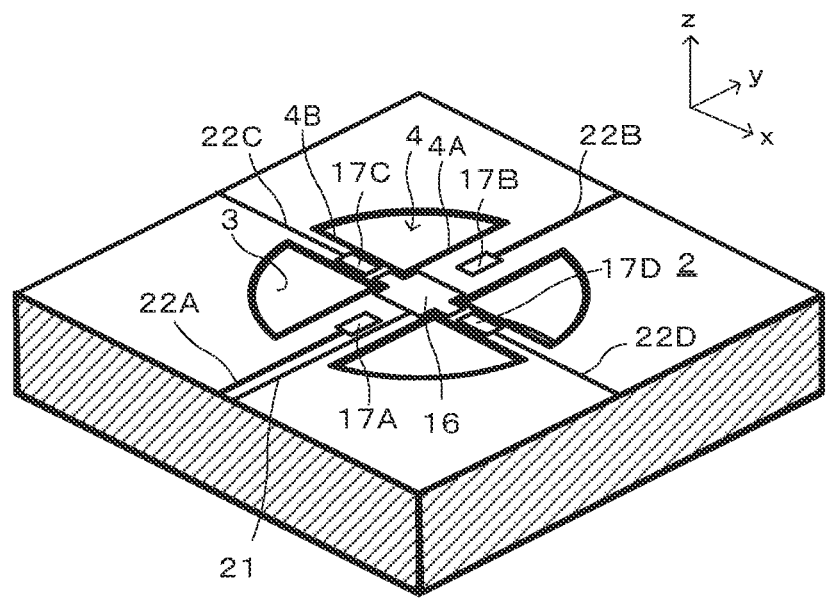
FIG. 14A is a perspective view (front) illustrating a fifth modified example of the substance detection element.
Figure 14B:
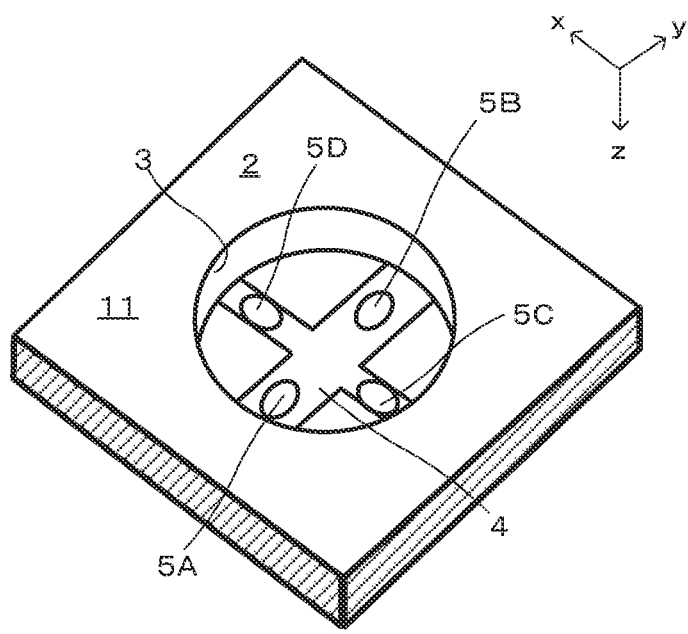
FIG. 14B is a perspective view (back) illustrating the fifth modified example of the substance detection element.

Further, the beam 4 may include the first beam 4A and the second beam 4B, and the drive electrode 16 may be provided in a part where the first beam 4A intersects the second beam 4B, as illustrated in FIG. 14A and FIG. 14B. In this case, the pair of the substance adsorption film 5A and the detection electrode 17A respectively provided at the same position on the front and the back of the beam 4, and the pair of the substance adsorption film 5B and the detection electrode 17B respectively provided at the same position on the front and the back of the beam 4 may be provided on both sides of the first beam 4A viewed from the part where the first beam 4A intersects the second beam 4B, and a pair of a substance adsorption film 5C and a detection electrode 17C respectively provided at the same position on the front and the back of the beam 4, and a pair of a substance adsorption film 5D and a detection electrode 17D respectively provided at the same position on the front and the back of the beam 4 may be provided on both sides of the second beam 4B viewed from the part where the first beam 4A intersects the second beam 4B. Four types of substances can be detected for one through hole 3 when the substance adsorption films 5A to 5D adsorb substances different from one another.

Figure 15:
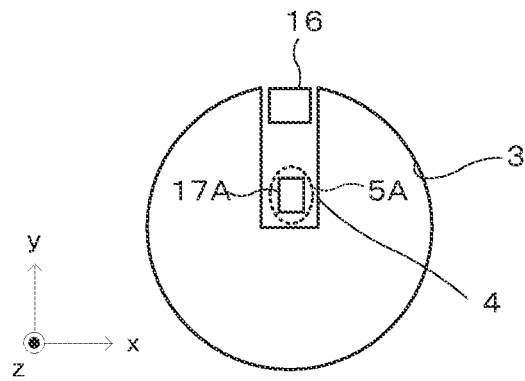
FIG. 15 is a plan view illustrating a sixth modified example of the substance detection element.

Further, the beam 4 may be a cantilever, as illustrated in FIG. 15. In this case, it is desirable to increase the vibration frequency of the beam 4 by increasing the width or the thickness of the beam 4. The drive electrode 16 may be placed at one end (one end fixed to the edge of a through hole 3) of the beam 4, and the detection electrode 17A may be placed at the center of the beam 4. The substance adsorption film 5A is provided on the back side of the detection electrode 17A.

Figure 16:
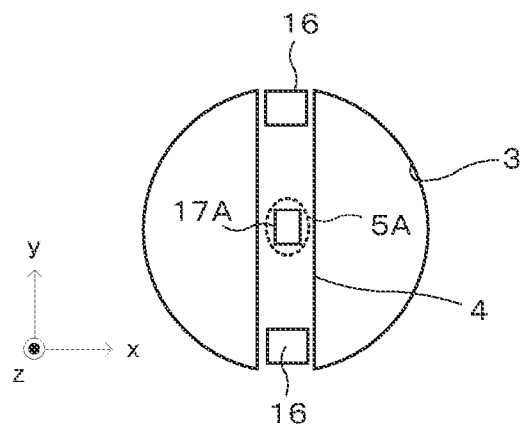
FIG. 16 is a plan view illustrating a seventh modified example of the substance detection element.

Further, when only one beam 4 is fixed to the edge of a through hole 3 at both ends in the longitudinal direction as illustrated in FIG. 16, it may be sufficient to provide the drive electrodes 16 at both ends of the beam 4 and provide the pair of the substance adsorption film 5A and the detection electrode 17A at the center of the beam 4.

Figure 17:
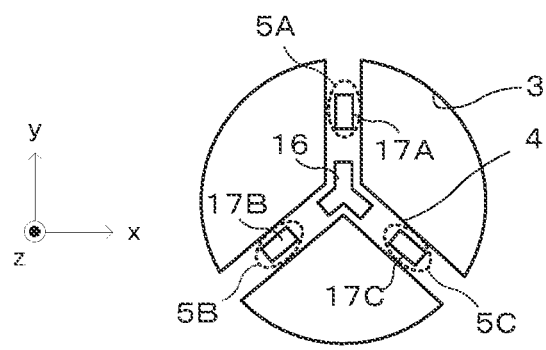
FIG. 17 is a plan view illustrating an eighth modified example of the substance detection element.

Further, a beam 4 fixed to the edge of a through hole 3 at three spots may be used, as illustrated in FIG. 17. In this case, the drive electrode 16 may be placed at an intersecting position of the beam 4, and the pair of the substance adsorption film 5A and the detection electrode 17A, the pair of the substance adsorption film 5B and the detection electrode 17B, and the pair of the substance adsorption film 5C and the detection electrode 17C may be respectively placed on three beams of the beam 4.

The first beam 4A is orthogonal to the second beam 4B, according to the aforementioned embodiment. Thus, the second beam 4B does not interfere with vibration of the first beam 4A. However, the first beam 4A does not need to be orthogonal to the second beam 4B and has only to intersect the second beam 4B.

According to the aforementioned embodiment, a constituent substance constituting a chemical substance is desorbed from the substance adsorption film 5A or 5B by vibrating the beam 4, in an environment in which the constituent substance does not exist in the vicinity before or after detection of the chemical substance. Thus, the substance detection element 1 can be reused without providing the substance detection element 1 with refreshing gas or providing means, such as a heater, for desorbing constituent substances from the substance adsorption films 5A and 5B in the substance detection element 1. Consequently, a device detecting a substance and being simple and compact as a whole can be provided.

Desorption of a constituent substance by vibration of the beam 4 can be also achieved by a substance detection element 1 having a structure as illustrated in FIG. 18. The substance detection element 1 also includes a supporting substrate 2, a plate-shaped beam 4 provided with a piezoelectric element 15 (see FIG. 5A), both ends of the beam 4 being supported by the supporting substrate 2, and a substance adsorption film 5E being provided on the beam 4 and changing the vibration frequency of the beam 4 by adhesion of a substance. The substance adsorption film 5E is provided across one entire surface of the beam 4 in the substance detection element 1. Furthermore, the substance detection element 1 includes drive electrodes 16 (see FIG. 5A) vibrating the beam 4 by applying voltage to the piezoelectric element 15 and detection electrodes 17A and 17B (see FIG. 5B) detecting information about the vibration frequency of the beam 4. The drive electrodes 16 and the detection electrodes 17A and 17B are provided on the back side of the region where the substance adsorption film 5E is provided.

As illustrated in FIG. 18, vibration of the beam 4 is started at a point t1. A constituent substance adsorbing to the substance adsorption film 5E before measurement is desorbed by the vibration in an initialization period T1, and the substance adsorption film 5E is initialized.

In a period T2 from a point t2 to a point t3, detection of a chemical substance is performed. The vibration of the beam 4 continues past the point t2. At the point t2, the substance detection element 1 is placed in a flow of gas being a detection target. A constituent substance constituting a chemical substance included in the gas passing through the through hole 3 thereby adsorbs to the substance adsorption film 5E.

In the period T2, the signal processing circuit 20 inputs voltage signals output from the detection electrodes 17A and 17B and detects a change in the vibration frequency of the beam 4, that is, adsorption of the constituent substance to the substance adsorption film 5E relating to the beam 4, based on the input voltage signals.

At the point t3, the substance detection element 1 is removed from the flow of the gas. The detection of a chemical substance thereby ends. However, in a period T3 from the point t3 to a point t4, the signal processing circuit 20 continues the vibration of the beam 4. The constituent substance thereby desorbs from the substance adsorption film 5E.

When performing desorption, the drive electrode 16 desorbs the constituent substance by vibrating the beam 4 in a film thickness direction of the substance adsorption film 5E. Thus, the desorbing direction of the constituent substance can be aligned to the vibration direction of the beam 4, and therefore the constituent substance can be easily desorbed. On the other hand, in a quartz crystal microbalance (QCM) based detection device using a crystal element as a substance adsorption film, the crystal element vibrates in a horizontal direction with respect to the film, and therefore a constituent substance is less likely to desorb by vibration.

According to the aforementioned embodiment, a frequency and intensity of a voltage signal provided for the drive electrodes 16 in the periods T1, T2, and T3 are constant. However, the present disclosure is not limited to the above. The frequency and the intensity of the voltage signal may be increased or decreased in the periods T1 and T3 as long as desorption of a constituent substance is accelerated. For example, the voltage signal in the period T1 and T3 may have a frequency different from that in the period T2, or the electric signal may have intensity different from that in the period T2.

While each of the number of through holes 3 and the number of beams 4 is seven, according to the aforementioned embodiment, the present disclosure is not limited thereto. Each of the number of through holes 3 and the number of beams 4 may be six or less or may be eight or more. The number of through holes 3 and the number of beams 4 can be determined according to the number of constituent substances being detection targets.

A through hole 3 is circular, according to the aforementioned embodiment. However, the present disclosure is not limited to the above. A through hole may be elliptic or rectangular, or the outer diameter may be a combination of a curve and a straight line.

Further, while a substance being a detection target is assumed to be an odor-constituting chemical substance, according to the aforementioned embodiment, the present disclosure is not limited thereto. For example, an odorless chemical substance included in gas may be detected.

Further, while a substance being a detection target is assumed to be a chemical substance included in gas, according to the aforementioned embodiment, the present disclosure is not limited thereto. The present disclosure is also applicable to detection of a substance in liquid.

Further, while the substance detection element 1 is assumed to be manufactured by use of an SOI wafer, according to the aforementioned embodiment, the present disclosure is not limited thereto. The substance detection element may be manufactured by use of another wafer.

While the lower electrode layer 14 and the piezoelectric element 15 are assumed to be provided across almost the entire surface of the beam 4, according to the aforementioned embodiment, the present disclosure is not limited thereto. The lower electrode layer 14 and the piezoelectric element 15 may be provided only in a part where the drive electrodes 16 and the detection electrodes 17A and 17B are formed.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

This application claims the benefit of Japanese Patent Application No. 2018-182353, filed on Sep. 27, 2018, and Japanese Patent Application No. 2019-80654, filed on Apr. 22, 2019, of which the entirety of the disclosures is incorporated by reference herein.

INDUSTRIAL APPLICABILITY

The present disclosure is applicable to detection of a chemical substance included in fluid.

REFERENCE SIGNS LIST

1 Substance detection element
2 Supporting substrate
3 Through hole
4 Beam
4A First beam
4B Second beam
5A, 5B, 5C, 5D, 5E Substance adsorption film
10 Base
11 Si supporting layer
12 Si active layer
13 Opening
14 Lower electrode layer
15 Piezoelectric element
16 Drive electrode
17A, 17B, 17C, 17D Detection electrode
20 Signal processing circuit
21 Drive signal line
22A, 22B Detection signal line

The invention claimed is:

1. A substance detection element comprising:
   a supporting substrate;
   a plate-shaped beam provided with a piezoelectric element, at least one end of the beam being fixed to the supporting substrate;
   a detection electrode detecting information about a vibration frequency of the beam; and
   a substance adsorption film changing a vibration frequency of the beam by adhesion of a sub stance,
   wherein the substance adsorption film and the detection electrode are respectively provided at a same position on a front and a back of the beam.

2. The substance detection element according to claim 1, wherein
   the supporting substrate is provided with a through hole, and
   the beam extends from an edge of the through hole toward a facing edge in such a way as to cover part of the through hole.

3. The substance detection element according to claim 2, wherein the beam is fixed to an edge of the through hole at least two spots, a plurality of pairs of the substance adsorption film and the detection electrode respectively provided at a same position on a front and a back of the beam is provided on the beam, and a substance absorbed by the substance absorption film is different for the each pair.

4. The substance detection element according to claim 3, wherein the beam is fixed to an edge of the through hole at both ends in a longitudinal direction of the beam, and pairs of the substance adsorption film and the detection electrode respectively provided at a same position on a front and a back of the beam are provided on both sides viewed from a center of the beam.

5. The substance detection element according to claim 4, wherein drive electrodes each vibrating the beam by applying voltage to the piezoelectric element are provided at both ends of the beam.

6. The substance detection element according to claim 5, wherein the drive electrode desorbs a substance adhering to the substance adsorption film by vibrating the beam.

7. The substance detection element according to claim 6, wherein the drive electrode vibrates the beam in a film thickness direction of the substance adsorption film.

8. The substance detection element according to claim 4, wherein a drive electrode vibrating the beam by applying voltage to the piezoelectric element is provided at a center of the beam.

9. The substance detection element according to claim 3, wherein the beam includes:

a first beam fixed to an edge of the through hole at both ends in a longitudinal direction; and a second beam being fixed to an edge of the through hole at both ends in a longitudinal direction and intersecting the first beam.

10. The substance detection element according to claim 9, wherein pairs of the substance adsorption film and the detection electrode respectively provided at a same position on a front and a back of the beam are provided on both sides of the second beam viewed from a part where the first beam intersects the second beam.

11. The substance detection element according to claim 9, wherein pairs of the substance adsorption film and the detection electrode respectively provided at a same position on a front and a back of the beam are provided on both sides of the first beam viewed from a part where the first beam intersects the second beam.

12. The substance detection element according to claim 10, wherein drive electrodes each vibrating the beam by applying voltage to the piezoelectric element are provided at both ends of the first beam.

13. The substance detection element according to claim 10, wherein a drive electrode vibrating the beam by applying voltage to the piezoelectric element is provided in a part where the first beam intersects the second beam.

14. The substance detection element according to claim 9, wherein a width of the first beam is set to be greater than a width of the second beam.

15. The substance detection element according to claim 9, wherein the first beam is orthogonal to the second beam.

* * * * *